US006735529B1

(12) United States Patent
Wald et al.

(10) Patent No.: US 6,735,529 B1
(45) Date of Patent: May 11, 2004

(54) PREDICTIVE TEST FOR PRE-ECLAMPSIA

(75) Inventors: Nicholas John Wald, London (GB); Christopher Redman, Oxford (GB)

(73) Assignees: Queen Mary & Westfield College, London (GB); University of Oxford, Oxford (GB)

( * ) Notice: Subject to any disclaimer, the term of this patent is extended or adjusted under 35 U.S.C. 154(b) by 0 days.

(21) Appl. No.: 09/719,055

(22) PCT Filed: Jun. 9, 1999

(86) PCT No.: PCT/GB99/01828
§ 371 (c)(1),
(2), (4) Date: Jun. 6, 2001

(87) PCT Pub. No.: WO99/64860
PCT Pub. Date: Dec. 16, 1999

(30) Foreign Application Priority Data

Jun. 9, 1998 (GB) ................................................ 9812432

(51) Int. Cl.[7] .......................... G06F 19/00; A61K 49/00
(52) U.S. Cl. .......................................... 702/19; 424/9.1
(58) Field of Search .............................. 702/19; 424/9.1

(56) References Cited

U.S. PATENT DOCUMENTS 5,712,103 A 1/1998 Leavitt et al.

FOREIGN PATENT DOCUMENTS

| WO | WO 90/07122 | 6/1990 |
| WO | WO 98/02751 | 1/1998 |
| WO | WO 98/28006 | 7/1998 |

OTHER PUBLICATIONS

Boffa, M.–C., et al., "Predictive value of plasma thrombomodulin in preeclampsia and gestational hypertension," *Chem. Abstracts 129:494*, Abstract No. 26642t, Chemical Abstracts Service (1998).

Kyle, P.M., et al., "A comparison of the inactive urinary kallikrein: Creatinine ratio and the angiotensin sensitivity test for the prediction of pre–eclampsia," *Chem. Abstracts 126:474*, Abstract No. 4166b, Chemical Abstracts Service (1997).

Marinoff, D.N., et al., "Utility of a single plasma fibronectin level for the prediction of preeclampsia," *Chem. Abstracts 123:799*, Abstract No. 166819g, Chemical Abstracts Service (1995).

Muttukrishna, S., et al., "Activin A and inhibin A as possible endocrine markers for pre–eclampsia," *Chem. Abstracts 127:467*, Abstract No. 32396r, Chemical Abstracts Service (1997).

Perez–Blanco, F.J., et al., "Urinary N–acetyl–β–glucosaminidase in the prediction of preeclampsia," *Chem. Abstracts 129:515*, Abstract No. 187926d, Chemical Abstracts Service (1998).

Derwent World Patents Index, English language abstract for RU 2107916, Derwent World Patents Index Accession No. 98–607817.

*Primary Examiner*—John S. Brusca
(74) *Attorney, Agent, or Firm*—Sterne, Kessler, Goldstein & Fox P.L.L.C.

(57) ABSTRACT

A method is provided which enables a prediction to be made about the risk of a pregnant woman developing pre-eclampsia which comprises an analysis of the serum levels of screening markers, Inhibin A and free β-hCG. Apparatus for carrying out the determination of the risk of developing pre-eclampsia based on the analysis of the serum samples is also provided.

14 Claims, 7 Drawing Sheets

PREDICTIVE TEST FOR PRE-ECLAMPSIA

CROSS REFERENCE TO RELATED APPLICATIONS

The present application is the National Stage of International Application No. PCT/GB99/01828, filed Jun. 9, 1999, which was published in English, on Dec. 16, 1999 as WO 99/64860; and claims priority to the filing date of Great Britain Application No. GB 9812432.4, filed Jun. 9, 1998.

BACKGROUND OF THE INVENTION

1. Field of the Invention

The present invention relates to a test which can be used to predict pre-eclampsia in pregnant women.

2. Related Art

Pre-eclampsia is a disorder of human pregnancy. Which affects around 5 to 10% of pregnancies. The underlying cause of pre-eclampsia remains unclear in spite of extensive clinical and basic research. Pre-eclampsia is the definition given to the condition in pregnancy in which elevated blood pressure is associated with proteinuria. Pre-eclampsia is distinct from eclampsia which is additionally associated with convulsions. Pre-eclampsia is defined in Souhami & Moxham *Textbook of Medicine*, Second edition, Churchill Livingstone (1994), as an abnormal rise in blood pressure between the first and second halves of pregnancy of ≦30/20 mmHg, with abnormal urate levels of >0.35 mmol/l at 32 weeks or >0.4mmol/l thereafter, associated with proteinuria, impaired renal function and clotting disorders. The consequences of pre-eclampsia are serious and include reduced uteroplacental perfusion, foetal growth retardation, pre-term birth, and increased foetal and maternal morbidity and mortality.

There have been many attempts to provide a reliable predictive test for pre-eclampsia. Previous suggestions have involved assays for the levels of circulating biochemical markers in the mother's blood but to date the scientific literature on this issue is contradictory and inconclusive. The following hormones have all been identified as possible markers in an elevation of levels might be predictive of pre-eclampsia in maternal plasma: progesterone, oestradiol, total human chorionic gonadotrophin (hCG), corticotrophin-releasing factor (CRF), adrenocorticotrophin (Muller et al *Am. J. Obst. Gynecol.* 175 37–40 (1996); Ashour et al *Am. J. Obst. Gynecol.* 176 438–444 (1997); Hsu et al *Am. J. Obst. Gynecol.* 170 1135–1138 (1994); Wenstrom et al *A. J. Obst. Gynecol.* 171 1038–1041 (1994)). Conversely, levels of oestriol, human placental lactogen and cortisol are unchanged or decreased. Whilst circulating CRF has been proposed as a prognostic marker for pre-eclampsia, treatment of hypertension does not influence maternal CRF levels and nor has any correlation been found between CRF levels and mean blood pressure.

Other possible markers which have been suggested are Activin A and Inhibin A. Activin is a hypophysiotrophic factor produced by the placenta which is know to act as a growth factor having activity in modulating cell growth and differentiation. Currently, there are three forms of activin which are recognised to exist as homodimeric proteins: Activin A ($\beta_A\beta_A$). Activin AB ($\beta_A\beta_B$) and Activin B ($\beta_B\beta_B$) in which the subunits are linked by disulphide bridges. Inhibins are heterodimeric proteins consisting of $\alpha\beta_A$ (Inhibin A) and $\alpha\beta_B$ (Inhibin B) subunits also linked by disulphide bridges. Additionally monomeric Inhibin $\alpha$ subunits are present in the circulation and follicular fluid. Inhibin is thought to have an endocrine role which inhibits pituitary production of follicle-stimulating hormone (FSH). Muttikrishna et al (*The Lancet* 349 1285–1288 (1997)) have proposed that Activin A and Inhibin A might be suitable markers for the onset of pre-eclampsia. These proteins were suggested because they were thought to be more sensitive markers than hCG or corticotrophin-releasing hormone where there is a considerable overlap in elevated hormone levels between control and pre-eclamptic women.

BRIEF SUMMARY OF THE INVENTION

However, it has now been found that a predictive test for pre-eclampsia which is based on levels of free β-human chorionic gonadotrophin (free β-hCG) and Inhibin A can in fact provide a surprisingly improved level of predictiveness over previously known tests. The present invention describes a system of screening for pre-eclampsia, in which a single risk estimate is derived from measurements carried out on biochemical samples obtained during pregnancy.

DETAILED DESCRIPTION OF THE INVENTION

According to a first aspect of the invention there is provided a method of predicting the risk of pre-eclampsia in a pregnant woman, the method comprising the steps of:

(a) obtaining a sample of blood from the woman;

(b) subsequently assaying the sample for the levels of free β-human chorionic gonadotrophin (free β-hCG) and Inhibin A present in the sample; and (c) determining the risk of pre-eclampsia using the measured levels of free β-human chorionic gonadotrophin (free β-hCG) and Inhibin A present in the sample.

Methods according to the present invention are carried out ex vivo. In the step (a), the sample of blood may be collected by any suitable means from the pregnant woman. The species free β-human chorionic gonadotrophin (free β-hCG) is distinct from the intact or total form of the molecule which is referred to simply as hCG or total hCG. The assay of the sample in step (b) for the levels of free β-human chorionic gonadotrophin (free β-hCG) and Inhibin A present in the sample may be carried out using standard protocols e.g. those based on ELISA (Enzyme-Linked ImmnoSorbent Assay) or RIA (RadioImmunoAssay), or commercially available kits, e.g. free β-human chorionic gonadotrophin (free β-hCG) can be measured using the solid phase, two site fluoroimmunometric assay based on a direct sandwich technique as described by Stevenson et al (*Ann. Clin. Biochem.* 30 99–100 (1993)) and Spencer et al (*Ann. Clin. Biochem.* 29 506–518 (1992)). Inhibin A can be measured according to the solid phase sandwich ELISA assay described by Groome et al (*J. Immunol. Methods* 165 167–176 (1993); *Clin. Endocrinol.*, 40 717–723 (i994)). In particular embodiments of the present invention, the assay may also comprise an analysis of the levels of unconjugated oestriol (uE$_3$), which can be measured using the solid phase, time resolved fluoroimmunoassay described in U.S. Pat. No. 4,565,790 and U.S. Pat. No. 4,808,541. Additionally, since free β-hCG and total hCG are known to be highly correlated in pregnancy, total hCG may also be used as a screening marker for pre-eclampsia in a method according to the present invention as an alternative to free β-hCG. The intact hCG molecule (total hCG) can be measured directly using exactly the same method as for the free β-subunit with AFP, i.e. sold phase, two-site fluoroimmunometric assay based on a direct sandwich technique. Preferably, the markers used are free β-hCG and Inhibin A measured after 20 weeks of pregnancy, and particularly at the end of the second trimester and the beginning of the third trimester.

In step (c), the determination of the risk of pre-eclampsia can be undertaken by comparing the levels of free β-human chorionic gonadotrophin (free β-hCG) and Inhibin A present in the sample with those in a control sample, or the median level in a group of control samples, i.e. samples from unaffected pregnancies, to provide a prediction of the probability of the onset of pre-eclampsia in the woman. The determination of risk nay comprise deriving the likelihood ratio using a multivariate analysis based on distribution parameters from a set of reference data.

Calculation of risk from the measured marker levels is based on the observed relative frequency distribution of marker levels in (a) pre-eclamptic and (b) unaffected pregnancies. Any of the known statistical techniques may be used. Preferably the multivariate Gaussian model is used, which is appropriate where the observed distributions are reasonably Gaussian. Such multivariate Gaussian analysis is in itself known, for example from Wald N J, Cuckle H S, Densem J W, et al (1988); Maternal serum screening for Down's syndrome in early pregnancy. BMJ 297, 883–887 and Royston P, Thompson S G (1992); Model-based screening by risk with application to Down's syndrome. Stat Med 11, 256–268.

In a preferred method, two Gaussian heights are calculated, (a) one for the pre-eclamptic distribution and (b) the other for the unaffected distribution. For this calculation, the necessary statistical parameters which specify the Gaussian distributions are the mean, the standard deviation and the correlations for the two distributions. The distributions are stored as reference data for use in analysis. The ratio of the two Gaussian heights gives the likelihood ratio which is a measure of the increased risk of having a disorder, given a particular combination of lest results, compared to the background risk, i.e. the risk in the absence of test results.

The estimation of risk consists of multiplying the likelihood ratio by the background risk for pre-eclampsia. The estimated risk is classified as screen-positive or screen negative based on a comparison with a predetermined risk cut-off. The value of the risk cut-off may be altered to vary the detection rate and false positive rate.

Methods in accordance with the present invention may further comprise the step (d) of re-expressing each measured screening marker level as a multiple of the median level of the respective screening marker in unaffected pregnancies of the same gestational age as the fetus of the pregnant woman. The screening marker levels may also be adjusted to allow for one or more factors selected from the group of maternal race, maternal weight, multiple birth and diabetic status.

According to a second aspect of the present invention there is provided an apparatus for determining whether a pregnant woman is at an increased risk of pre-eclampsia, the apparatus comprising:
(a) data input means for inputting a measurement of the serum levels of Inhibin A and free β-human chorionic gonadotrophin (free β-hCG) in a sample obtained from said pregnant woman; and
(b) calculation means for determining the risk of pre-eclampsia using the input levels of the serum markers Inhibin A and free β-human chorionic gonadotrophin (free β-hCG).

In certain embodiments of the invention, the calculation means may be arranged to determine the risk of pre-eclampsia by deriving the likelihood ratio for pre-eclampsia using a multivariate analysis based on distribution parameters derived from a set of reference data. Preferably the multivariate analysis is a multivariate Gaussian analysis.

Apparatus in accordance with this aspect of the invention may further comprise (c) means for re-expressing the levels of each input screening marker Inhibin A and free β-human chorionic gonadotrophin (free β-hCG) as a multiple of the median level of the respective screening marker in unaffected pregnancies of the same gestational age as the fetus of the pregnant women and supplying the re-expressed screening marker levels to said calculation means.

According to a third aspect of the present invention there is provided a method of operating an apparatus as described in accordance with the second aspect to determine the risk of pre-eclampsia in a pregnant woman. The data input means may be used to enter items of data identified as the concentrations of serum markers Inhibin A and free β-human chorionic gonadotrophin (free β-hCG) in a sample obtained from a pregnant woman. The calculation means may be used to calculate the risk of pre-eclampsia using the input levels of the serum markers. The operation the different steps and preferred features are as described above. In another preferred embodiment of this aspect of the invention, the method comprises the steps described in FIGS. 4, 5, 6 and 7.

According to a fourth aspect of the invention there is provided a kit for predicting the onset of pre-eclampsia in a pregnant woman, comprising means for assaying a sample from the women for the levels of free β-human chorionic gonadotrophin (free β-hCG) and Inhibin A present in the sample.

Preferred features for the second and subsequent aspects of the invention are as for the first aspect *mutatis mutandis*.

BRIEF DESCRIPTION OF THE DRAWINGS

The invention will now be further described by way of reference to the following Examples and Figures which are provided for the purposes of illustration only and are not to be construed as being limiting on the invention. Reference is made to a number of Figures in which.

EXAMPLES

Example 1

Serum Analysis

Serum analysis was carried out on serum collected between 1973 and 1975 from the John Radcliffe Maternity Hospital, Oxford, United Kingdom. Pre-eclampsia was defined as (i) a rise in systolic and diastolic pressure during pregnancy of 30 and 20 mm of mercury respectively, compared with the level found at the first antenatal booking visit; (ii) proteinuria greater than 10 mg % in a mid-stream urine sample; (iii) renal impairment as judged by the elevation of plasma uric acid levels of 6 mg % or more. Nineteen women bad blood samples taken after 12 weeks gestation stored at −40° C. Nine women had one sample, seven had two samples, and three had three samples.

For each sample, three controls were identified selected at random from the patients attending the hospital who had provided a blood'sample at the same gestational age in the same calendar quarter and were the same age. Neither cases nor controls were associated with Down's Syndrome or neural tube defects. Serum alphafetoprotein (AFP) and free β-human chorionic gonadotrophin (hCG) were measured using the Wallac-Delfia™ kit, unconjugated oestriol ($uE_3$) using the Ortho Clinical Diagnostics kit, and Inhibin A using the assay kit produced by Serotec. One sample was sufficient only to measure Inhibin A. For each serum marker, the logs of the medians for the controls were plotted by gestational age and a regression line fitted. The predicted marker values for each gestational age were estimated. All markers were expressed as multiples of their predicted median values for the controls, i.e. MoM's.

All analyses were also completed by using the marker values for each case expressed as a multiple of the median value of its three controls. This removes the need to model the relationship of the markers with gestational age. The results did not differ significantly from those presented here.

The data were analysed using robust regression with the cluster option in STATA (Stata Corporation, Stata Statistical Software: Release 5.0, College Station, Tex. (1997)) to take account of repeat samples of some of the women. Table 1 shows the results for the four markers used, classified according to the onset of proteinuria. Inhibin A and free β-hCG values are raised in the pregnancies with pre-eclampsia and the level increases with decreasing time prior to proteinuria and is highest in women after the diagnosis of the disorder. Within three weeks of the onset of proteinuria, the mean Inhibin A value was 3.18 times the median for the controls (95% Confidence Interval—CI, 1.98–5.11), and the mean free β-hCG 3.43 (1.58–7.42). Even 10 weeks prior to the onset of proteinuria these two markers were elevated. The mean $uE_3$ was significantly reduced in the controls, within three weeks of the onset of proteinuria, MoM=0.51 (95% CI, 0.42–0.62), but appears to rise again after the onset of proteinuria.

Table 2 shows the observed and expected (using the log Gaussian model) number of affected pregnancies above specified Inhibin A and free β-hCG levels. The correspondence is good. Based on multivariate Gaussian model using the parameters in Table 3 (based on results prior to the onset of proteinuria) in combination they yield an approximately 40% detection rate for a 5% false-positive rate as shown in Tables 5a and 5b.

Using the parameters in Table 4 (based on serum samples collected at 20 weeks gestation or later and before the onset of proteinuria) the detection rate for a 5% false-positive rate is 57% using free β-hCG and Inhibin A, or 67% using free β-hCG, Inhibin A and $uE_3$, as shown in Tables 5c and 5d.

The reduction in $uE_3$ needs to be investigated in further studies. These estimates are tentative because they are based on small numbers but provide an indication of the potential use of Down's Syndrome screening markers in the prediction of pre-eclampsia. It provides the opportunity to undertake randomised prevention trials in women at high risk of pre-eclampsia identified at the time of screening for Down's Syndrome, or later in pregnancy.

Figure 1:
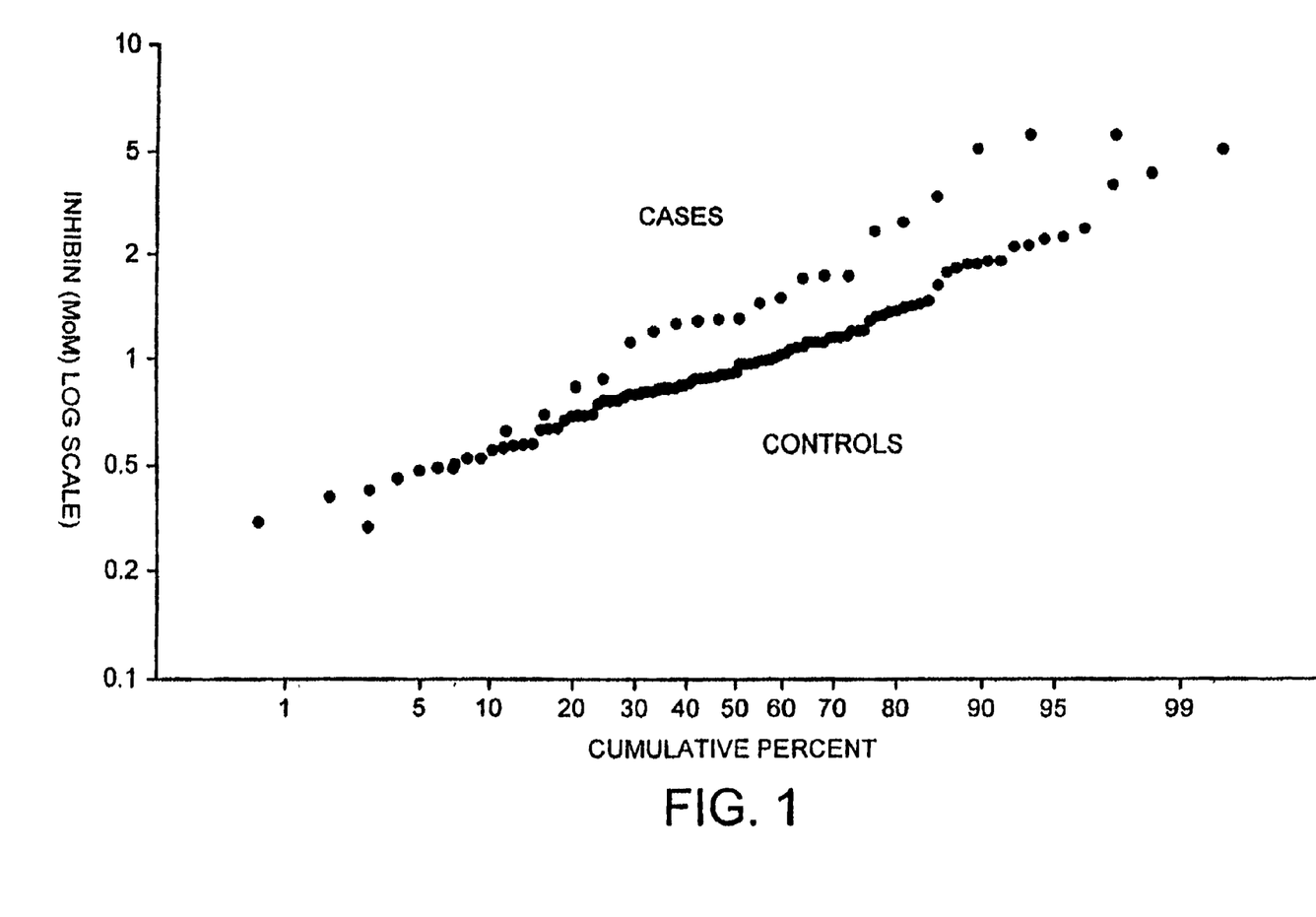
FIG. 1 shows a probability plot of the Inhibin levels in maternal serum in pre-eclampsia pregnancies (n=23) and unaffected pregnancies (n=96) collected before the onset of proteinuria. MoM=multiples of the normal median for unaffected pregnancies of the same gestational age.
Figure 2:
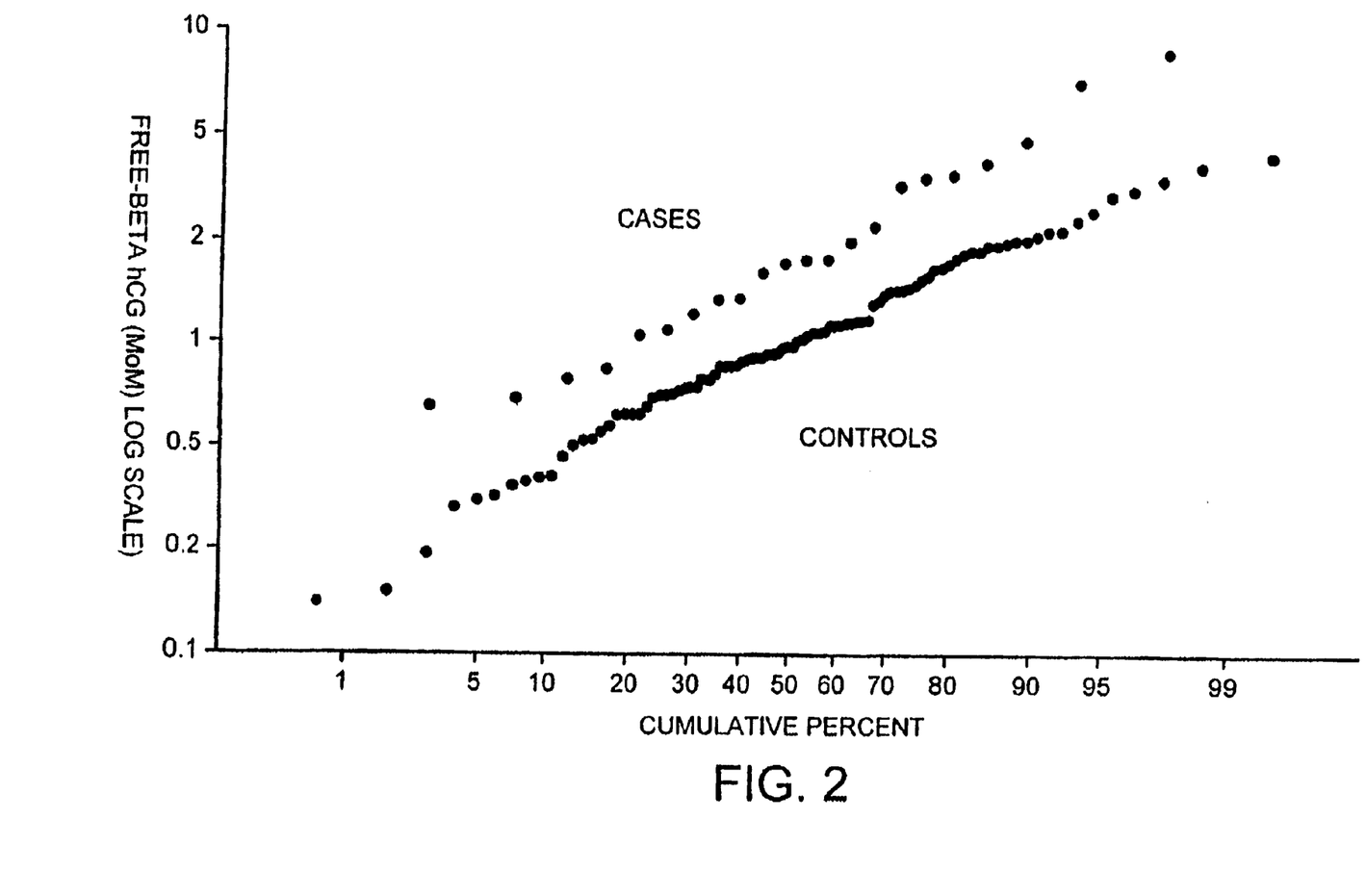
FIG. 2 shows a probability plot of the free β-hCG levels in maternal serum in pre-eclampsia pregnancies (n=22) and unaffected pregnancies (n=93). MoM=multiples of the normal median for unaffected pregnancies of the same gestational age.

The results show that Inhibin A and free β-hCG are useful second trimester serum markers for pre-eclampsia. Each provided some independent predictive information because they were not totally correlated. FIGS. 1 and 2, and Table 2 demonstrate that both the Inhibin A and free β-hCG data fit log Gaussian distributions reasonably well.

Figure 3:
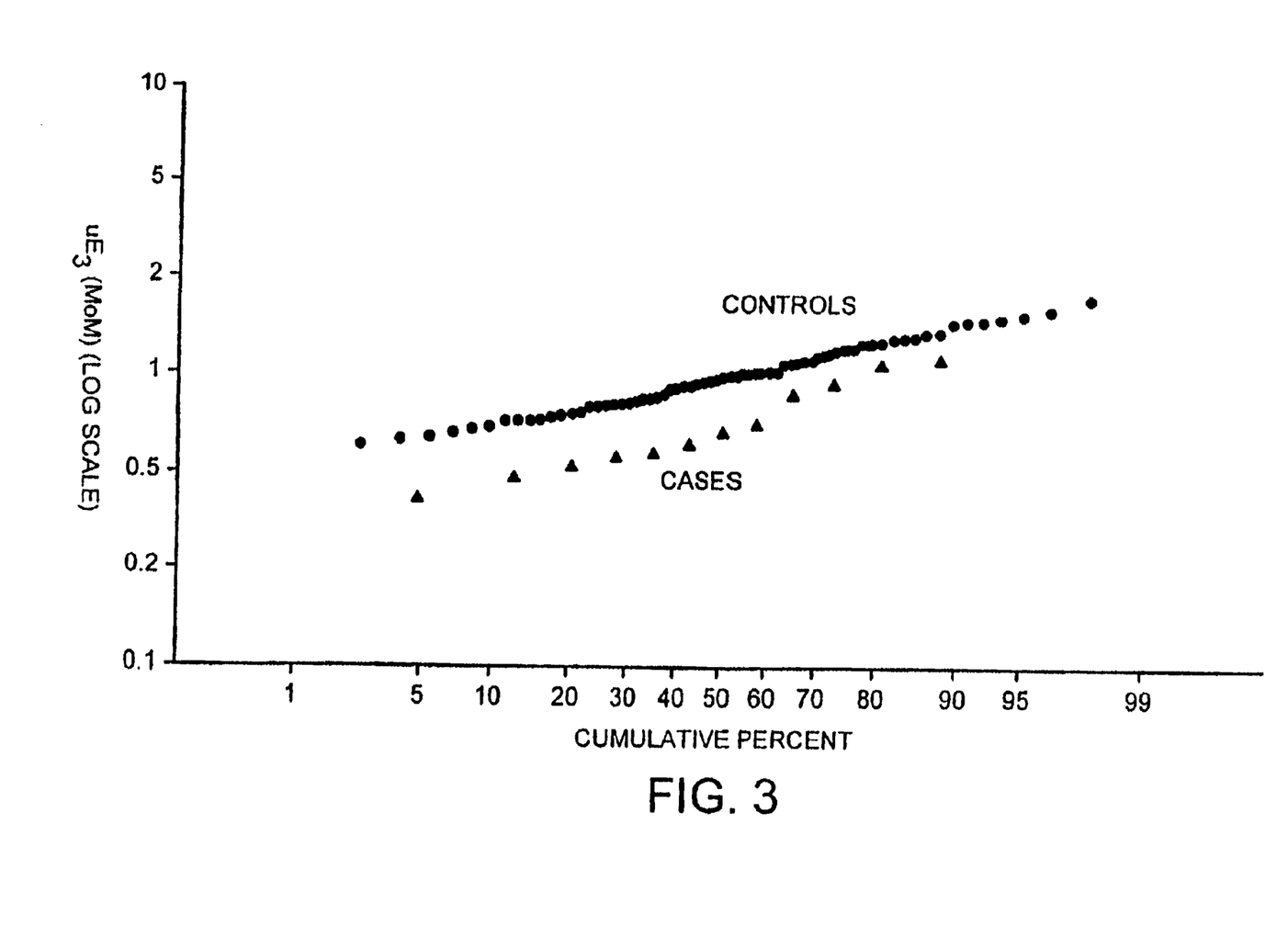
FIG. 3 shows a probability plot of the oestriol ($uE_3$) levels in maternal serum in pre-eclampsia pregnancies (n=13) and unaffected pregnancies (n=66). MoM=multiples of the normal median for unaffected pregnancies of the same gestational age.

The parameters in Tables 3 and 4 referred to above in Example 1 are calculated as follows. The mean $\log_{10}$ MoM in affected pregnancies is estimated from the $\log_{10}$ median value for each marker in affected pregnancies. The median MoM in unaffected pregnancies is 1.0 by definition, and so the $\log_{10}$ MoM value is 0. Standard deviations in affected and unaffected pregnancies are estimated from the slope of the regression lines fitted to the data in FIGS. 1, 2 and 3, between the $10^{th}$–$90^{th}$ centile range. Correlation coefficients between the markers in affected and unaffected pregnancies are estimated from the covariance between markers (after excluding values greater than 3.5 standard deviations from the mean), divided by the product of the standard deviations of the individual markers.

Example 2

Calculation of Risk from Measured Marker Levels

Most screening marker levels are known to vary with gestational age. To take account of this variation, each marker level may be expressed as a multiple of the median level (MoM) for unaffected pregnancies of the same gestational age. MoMs may be adjusted in a known way to take account of factors which are known to affect marker levels, such as maternal weight, ethnic group, diabetic status and the number of fetuses carried.

Calculation of risk from the measured marker levels is based on the observed relative frequency distribution of marker levels in (a) pre-eclamptic and (b) unaffected pregnancies. Any of the known statistical techniques may be used. Preferably the multivariate Gaussian model is used, which is appropriate where the observed distributions are reasonably Gaussian. Such multivariate Gaussian analysis is in itself known, for example from Wald N J, Cuckle H S, Densem J W, et al (1988); Maternal serum screening for Down's syndrome in early pregnancy. BMJ 297, 883–887 and Royston P, Thompson S G (1992); Model-based screening by risk with application to Down's syndrome Stat Med 11, 256–268. Thus no detailed discussion is necessary, but a summary is given as follows.

If a matrix representation is used, the height H of the Gaussian distribution for a given set of measured levels is given by the equation:

$$H = \frac{1}{\prod(\sigma) \cdot (2\pi)^{p/2} \cdot det(R)^{1/2}} \exp\left(\frac{-1}{2} \cdot Z^T \cdot R^{-1} \cdot Z\right)$$

where p is the number of markers, $\Pi(\sigma)$ is the product of the standard deviations for each distribution, Z is a matrix containing the measured level of each marker expressed in standard deviation units, namely ((measured level−mean)/standard deviation), and R is a matrix containing the correlations between the screening markers.

Two Gaussian heights are calculated, (a) one for the pre-eclamptic distribution and (b) the other for the unaffected distribution. For this calculation the necessary statistical parameters which specify the Gaussian distributions are the mean, standard deviation and correlations for the two distributions, as summarised in Table 4 (an improved set of parameters compared to the parameters given in Table 3) below for the preferred markers. The distribution parameters are stored as reference data for use in the analysis.

The ratio of the two Gaussian heights gives the likelihood ratio. The likelihood ratio is a measure of the increased risk of having a disorder, given a particular combination of test results, compared to the background risk (that is, the risk in the absence of the test results).

The likelihood ratio is multiplied by the known background risk, to calculate the improved estimate of risk. The estimated risk is classified as screen-positive or screen-negative based on a comparison with a predetermined risk cut-off. The value of the risk cut-off may be altered to vary the detection rate and false-positive rate.

Expected pre-eclampsia detection rates and false-positive rates using the present invention have been estimated using the method previously described in Wald N J, Cuckle H S, Densem T W, et al (1988) referred to above. Tables 5a and 5b show the performance of screening for pre-eclampsia before the onset of proteinuria, using free β-hCG and Inhibin-A, in terms of the detection rate achieved at specified false-positive rates, and the false-positive rate required to achieve specified detection rates. Tables 5c and 5d show the performance of screening for pre-eclampsia at 20 weeks gestation or later, and before the onset of proteinuria, in the same terms.

Example 3

Computer Algorithms for Risk Calculation

FIGS. 4 to 7 are flowcharts illustrating a specific method according to the present invention which is explained in detail below.

Figure 4:
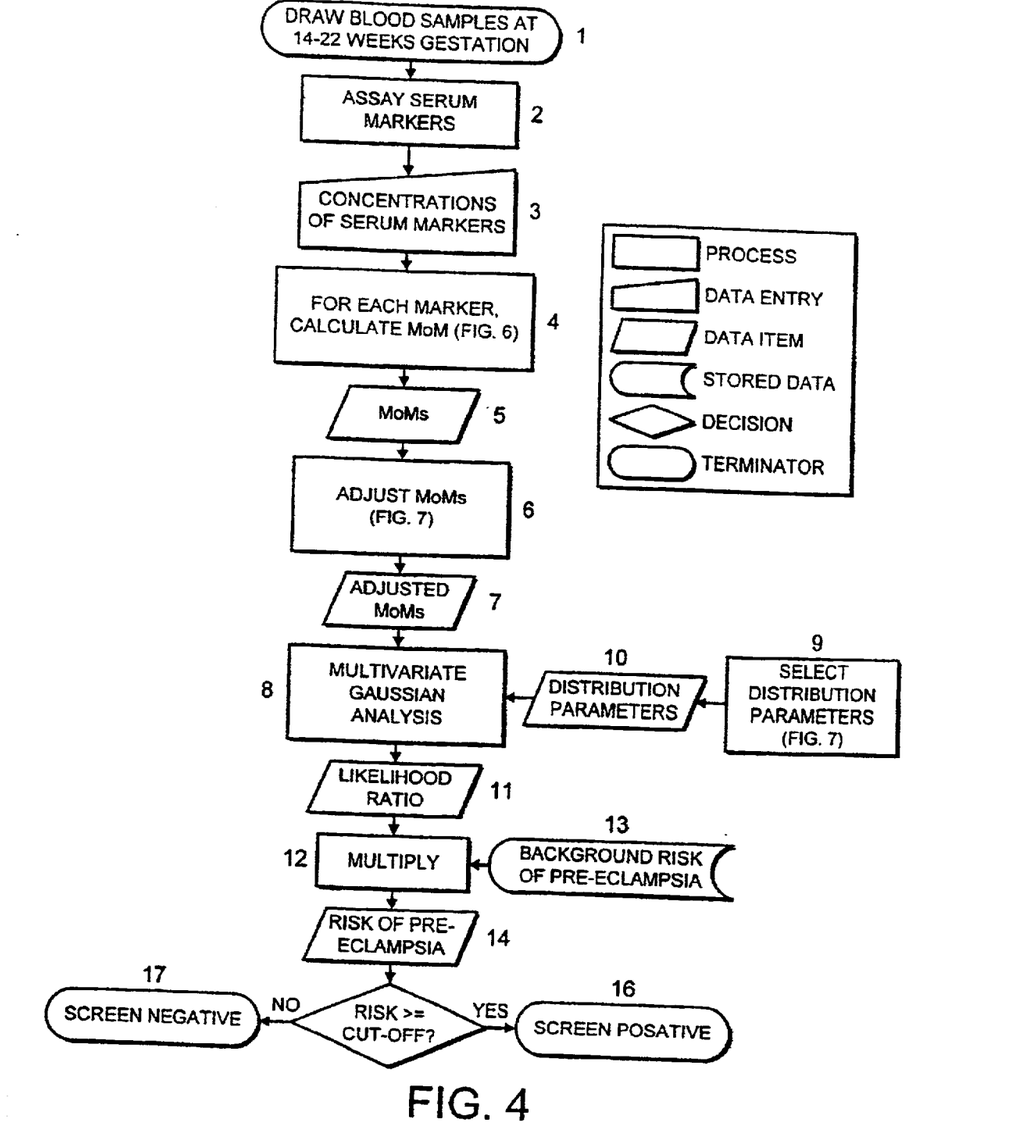
FIG. 4 shows a flowchart illustrating a screening method for pre-eclampsia that involves deriving a risk estimate from measurements made on biochemical samples collected during pregnancy.
Figure 5:
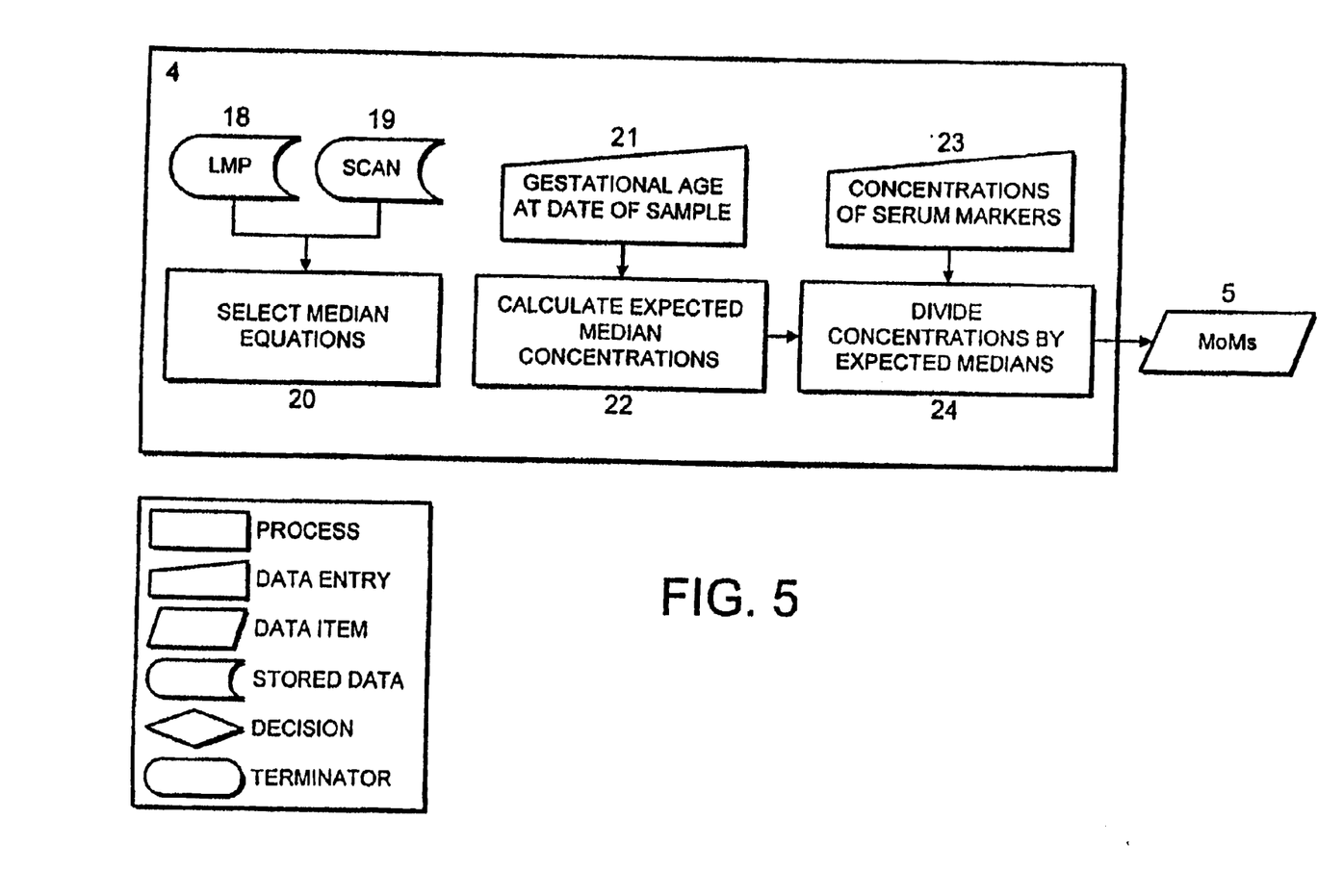
FIG. 5 shows a flowchart illustrating the procedure for calculating multiples of the median (MoM) for biochemical markers. LMP=last menstrual period.

In the second trimester of pregnancy at around 14 to 22 weeks, a blood sample is drawn in step 1. Subsequently in step 2, the sample is assayed for the biochemical markers selected.

The processing of the measurements taken in step 2 is described below, and may be automated by implementing it in hardware or software.

Data input means are used to input the concentrations (levels) of the biochemical markers in step 3. In step 4, each marker level is re-expressed as a multiple of the median (MoM) level for unaffected pregnancies of the same gestational age and output as data item 5. Step 4 is illustrated in more detail in FIG. 5. Stored data LMP 18 and scan 19 specific to respective methods of estimating gestational age are used to select an equation based on stored data which estimates the expected median concentrations for each marker at different gestational ages in step 20. Data LMP 18 is specific to estimation of gestational age based on the first day of the last menstrual period. Data scan 19 is specific to estimation of gestational age from an ultrasound measure of the fetus, usually a biparietal diameter (BPD) or crown-rump length (CRL) measurement. Based on an input in step 21 of the gestational age at the date of sample, for each marker in step 22 the expected median level in unaffected pregnancies of the same gestational age is calculated using the equation selected in step 20. In step 24 each marker level input in step 3 is divided by the expected median for that marker to output the MoM as data item 5.

Figure 6:
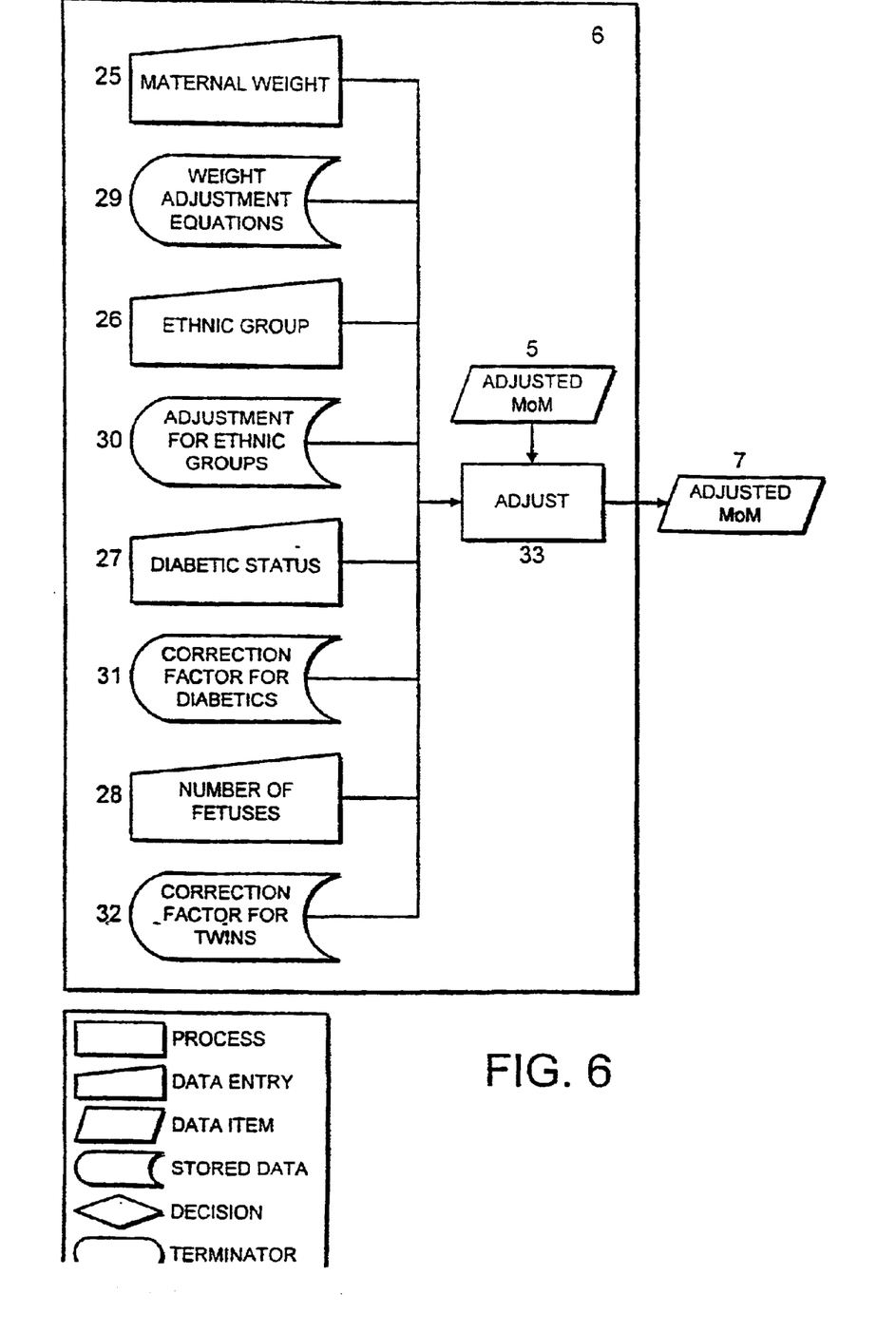
FIG. 6 shows a flowchart illustrating the procedure for adjusting MoM values to allow for various factors, other than gestational age, that may affect biochemical marker levels.
Figure 7:
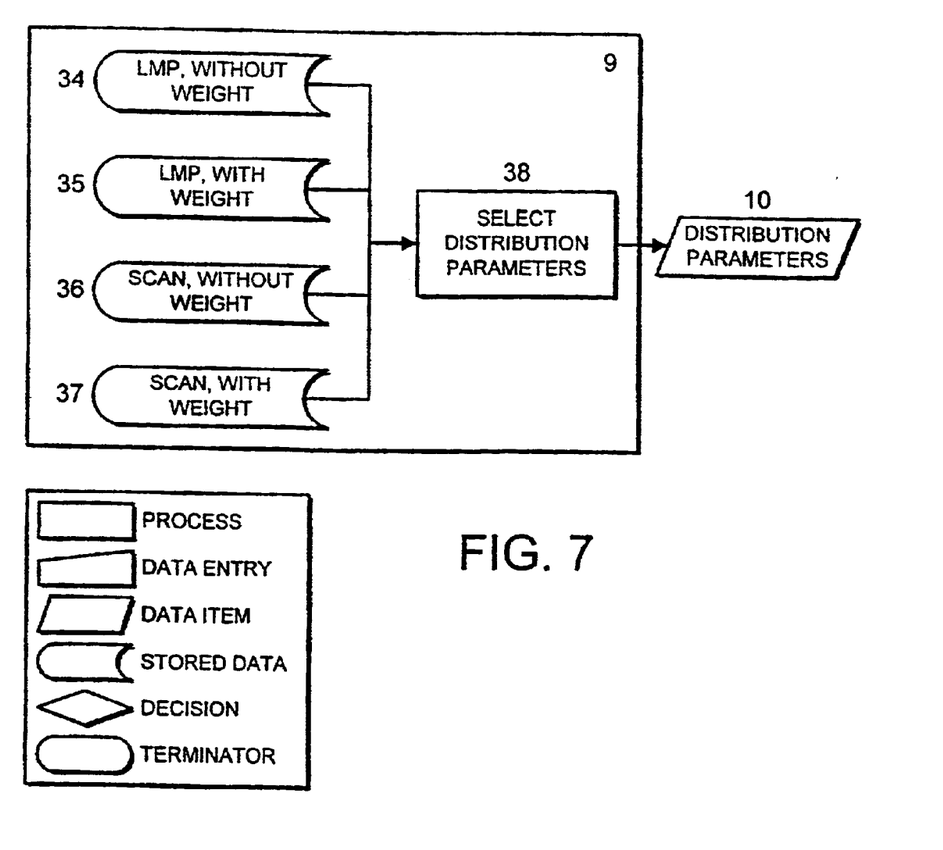
FIG. 7 shows a flowchart illustrating the procedure for selecting the appropriate parameters of the distributions of screening markers in affected and unaffected pregnancies. LMP=last menstrual period.

Optionally the MoMs 5 for the biochemical markers may be adjusted in step 6 which is illustrated in detail in FIG. 6. Based on an input of any one or more of maternal weight, ethnic group, diabetic status and the number of fetuses in steps 25 to 28, respectively, stored weight, adjustment equations 29, ethnic group adjustments 30, diabetes correction factors 31, and multiple birth correction factors 32 are used in step 33 to adjust the MoMs 5. The adjusted MoMs are output as data item 7.

In step 8, a multivariate Gaussian analysis of the MoMs is performed. For use in this analysis, distribution parameters 10 are selected in step 9 which is described in more detail in FIG. 7. For each marker the distribution parameters are stored as reference data 34 to 37 for different methods of estimating gestational age (LMP or scan) and based on whether or not the MoM has been adjusted for maternal weight. In step 38 the appropriate distribution parameters are selected and output as data item 10.

The multivariate Gaussian analysis 8 outputs a likelihood ratio as data item 11. In step 12 the likelihood ratio is multiplied by the stored background risk of pre-eclampsia 13 to output the estimated risk of pre-eclampsia as data item 14. The estimated risk 14 is compared with a predetermined cut-off in step 15 to produce a screen-positive result 16 when the risk is equal to or greater than the cut-off, or a screen-negative result 17 otherwise.

TABLE 1

Specified serum markers in pregnancies with pre-eclampsia according to timing of collection of serum samples relative to onset of proteinuria

| Collection of serum sample relative to onset of proteinuria | Median gestation of onset of proteinuria | No. of women | No. of samples | Median gestation of serum samples | Geometric Mean (MoM) values (95% CI) | | | |
|---|---|---|---|---|---|---|---|---|
| | | | | | Inhibin A | AFP | Free β-hCG | uE$_3$ |
| Over 11 weeks before | 29.9 | 10 | 10 | 12.1 | 1.00 (0.75–1.32) | 0.82 (0.61–1.11) | 1.29 (1.95–1.76) | 0.96 (0.48–1.94) |
| 10–4 weeks before | 29.4 | 6 | 6 | 21.5 | 1.26 (0.66–2.41) | 1.13 (0.78–1.64) | 2.09 (1.24–3.54) | 0.87 (0.67–1.14) |

TABLE 1-continued

Specified serum markers in pregnancies with pre-eclampsia according to timing of collection of serum samples relative to onset of proteinuria

| Collection of serum sample relative to onset of proteinuria | Median gestation of onset of proteinuria | No. of women | No. of samples | Median gestation of serum samples | Geometric Mean (MoM) values (95% CI) | | | |
|---|---|---|---|---|---|---|---|---|
| | | | | | Inhibin A | AFP | Free β-hCG | uE₃ |
| 3–0 weeks before* | 28.9 | 6 | 7† | 27.9 | 3.18 (1.98–5.11) | 1.60 (0.58–4.42) | 3.43 (1.58–7.42) | 0.51 (0.42–0.62) |
| Up to 3 weeks after proteinuria* | 29.9 | 5 | 9 | 32.3 | 6.66 (3.80–11.68) | 1.36 (0.63–2.95) | 3.98 (2.52–6.31) | 0.93 (0.66–1.29) |
| Total* | 29.9 | 19 | 32† | 23.4 | 2.27 (1.52–3.38) | 1.14 (0.83–1.57) | 2.34 (1.66–3.28) | 0.82 (0.60–1.12) |
| Total prior to onset proteinuria* | 29.8 | 16 | 23† | 21.1 | 1.49 (1.03–2.16) | 1.07 (0.76–1.52) | 1.92 (1.28–2.89) | 0.78 (0.54–1.13) |

MoM — multiples of the median
*Standard errors adjusted for more than one sample from some women
†One sample only had measurements of Inhibin

TABLE 2

Number and percentage of pregnancies with pre-eclampsia collected before onset of proteinuria and unaffected pregnancies according to Inhibin A and free β-hCG

| | Inhibin A | | | | Free β-hCG | | | |
|---|---|---|---|---|---|---|---|---|
| MoM | Affected no. (%) (n = 23) | Modelled* % | Unaffected no. (%) (n = 96) | Modelled* % | Affected no. (%) (n = 22) | Modelled* % | Unaffected no. (%) (n = 93) | Modelled* % |
| ≧0.5 | 21 (91%) | 93% | 87 (91%) | 90% | 22 (100%) | 97% | 79 (85%) | 84% |
| ≧1.0 | 17 (74%) | 70% | 42 (44%) | 50% | 18 (82%) | 82% | 46 (49%) | 50% |
| ≧1.5 | 11 (48%) | 50% | 18 (19%) | 22% | 13 (59%) | 63% | 29 (31%) | 28% |
| ≧2.0 | 6 (26%) | 35% | 13 (14%) | 9% | 9 (41%) | 48% | 17 (18%) | 16% |
| ≧2.5 | 6 (26%) | 25% | 5 (5%) | 4% | 7 (32%) | 36% | 7 (8%) | 9% |
| ≧3.0 | 4 (17%) | 18% | 3 (3%) | 2% | 7 (32%) | 27% | 5 (5%) | 5% |

*These percentages are estimated assuming both Inhibin A and free β-hCG have log normal distributions

TABLE 3

Distribution parameters of Inhibin A and free β-hCG in pregnancies with and without pre-eclampsia based on samples collected before onset of proteinuria (23 cases and 96 control samples)

| | | Log₁₀ MoM | |
|---|---|---|---|
| | | Inhibin A | Free β-hCG |
| Means | Unaffected | 0 | 0 |
| | Affected | 0.164 | 0.284 |
| Standard deviations | Unaffected | 0.234 | 0.297 |
| | Affected prior to onset of proteinuria | 0.332 | 0.317 |
| Correlation | Unaffected | | 0.198 |
| | Affected | | 0.899 |

TABLE 4

Standard deviations, correlation coefficients, and means (log₁₀ MoM) for selected screening markers in pregnancies with and without pre-eclampsia (affected and unaffected respectively); serum samples collected at 20 weeks gestation or later and prior to the onset of proteinuria (13 cases and 69 control samples)

| | Inhibin A | Free β-hCG | uE₃ |
|---|---|---|---|
| MEANS | | | |
| Free β-hCG | 0 | 0 | 0 |
| Inhibin-A | 0.312 | 0.389 | −0.164 |

TABLE 4-continued

Standard deviations, correlation coefficients, and means (log₁₀ MoM) for selected screening markers in pregnancies with and without pre-eclampsia (affected and unaffected respectively); serum samples collected at 20 weeks gestation or later and prior to the onset of proteinuria (13 cases and 69 control samples)

| | Inhibin A | Free β-hCG | uE₃ |
|---|---|---|---|
| STANDARD DEVIATIONS | | | |
| Unaffected | 0.217 | 0.304 | 0.138 |
| Affected | 0.282 | 0.339 | 0.200 |
| CORRELATION COEFFICIENTS | | | |
| Unaffected | | | |
| Free β-hCG | 0.276 | 0.206 | |
| uE3 | 0.037 | | |
| Affected | | | |
| Free β-hCG | 0.893 | −0.508 | |
| uE3 | −0.469 | | |

TABLE 5a

Performance of pre-eclampsia screening using free β-hCG and Inhibin-A before onset of proteinuria: detection rates according to specified false-positive rates

| False positive rate (%) | Detection rate (%). |
| --- | --- |
| 3 | 36 |
| 4 | 40 |
| 5 | 43 |
| 6 | 45 |
| 7 | 48 |
| 8 | 50 |

TABLE 5b

Performance of pre-eclampsia screening using free β-hCG and Inhibin-A before onset of proteinuria: false-positive rates according to specified detection rates

| Detection rate (%) | False-positive rate (%). |
| --- | --- |
| 30 | 1.8 |
| 40 | 4.2 |
| 50 | 8.2 |
| 60 | 14 |

TABLE 5c

Performance of pre-eclampsia screening using free β-hCG, Inhibin A and uE3 measured in serum samples collected at 20 weeks gestation or later and before the onset of proteinuria: detection rates according to specified false-positive rates

| False positive rate (%) | Detection rate (%) | |
| --- | --- | --- |
| | Free β-hCG and Inhibin A | Free β-hCG, Inhibin A and uE$_3$ |
| 3 | 50 | 62 |
| 4 | 54 | 64 |
| 5 | 57 | 67 |
| 6 | 60 | 69 |
| 7 | 62 | 70 |
| 8 | 64 | 72 |

TABLE 5d

Performance of pre-eclampsia screening using free β-hCG, Inhibin A and uE3 measured in serum samples collected at 20 weeks gestation or later and before the onset of proteinuria: detection rates according to specified false-positive rates

| Detection rate (%) | False-positive rate (%) | |
| --- | --- | --- |
| | Free β-hCG and Inhibin A | Free β-hCG, Inhibin A and uE$_3$ |
| 30 | 0.4 | 0.04 |
| 40 | 1.2 | 0.2 |
| 50 | 2.9 | 0.8 |
| 60 | 6.0 | 2.5 |
| 70 | 12 | 6.9 |
| 80 | 22 | 16 |

What is claimed is:

1. A method of predicting the risk of pre-eclampsia in a pregnant woman, the method comprising the steps of:
   (a) obtaining a sample of blood from the woman;
   (b) subsequently assaying the sample for the levels of free β-human chorionic gonadotrophin (free β-hCG), Inhibin A and unconjugated oestriol (uE$_3$) present in the sample; and
   (c) determining the risk of pre-eclampsia using the measured levels of free β-human chorionic gonadotrophin (free β-hCG), Inhibin A, and unconjugated oestriol (uE$_3$) present in the sample.

2. A method as claimed in claim 1, in which the method is carried out after 20 weeks of pregnancy.

3. A method as claimed in claim 2, in which the method is carried out at the end of the second trimester and the beginning of the third trimester.

4. A method as claimed in any of claims 1, 2 or 3, in which the determination of risk in step (c) is undertaken by comparing the levels of free β-human chorionic gonadotrophin (free β-hCG), Inhibin A and unconjugated oestriol (uE$_3$) present in the sample with those in a control sample.

5. A method as claimed in claim 4, in which the determination of risk comprises deriving the likelihood ratio using a multivariate analysis based on distribution parameters from a set of reference data.

6. A method as claimed in claim 5, in which the multivariate analysis is a multivariate Gaussian analysis.

7. A method as claimed in claim 6, in which the estimation of risk consists of multiplying the likelihood ratio by the background risk for pre-eclampsia.

8. A method as claimed in any one of claims 1 or 2 to 7, the method further comprising a step (d) of re-expressing the measured levels of β-human chorionic gonadotrophin (free β-hCG), Inhibin A, and unconjugated oestriol (uE$_3$) as a multiple of the median level of the measured levels, respectively of β-human chorionic gonadotrophin (free β-hCG), Inhibin A, and unconjugated oestriol (uE$_3$) in unaffected pregnancies of the same gestational age as the fetus of the pregnant woman.

9. A method as claimed in claim 8, in which the measured levels of β-human chorionic gonadotrophin (free β-hCG), Inhibin A, and unconjugated oestriol (uE$_3$) are adjusted to allow for one or more factors selected from the group of maternal race, maternal weight, multiple birth and diabetic status.

10. An apparatus for determining whether a pregnant woman is at an increased risk of pre-eclampsia, the apparatus comprising:
    (a) data input means for inputting a measurement of the serum levels of Inhibin A, free β-human chorionic gonadotrophin (free β-hCG) and unconjugated oestriol (uE$_3$) in a sample obtained from said pregnant woman; and
    (b) calculation means for determining the risk of pre-eclampsia using the input levels of the serum markers Inhibin A, free β-human chorionic gonadotrophin (free β-hCG) and unconjugated oestriol (uE$_3$).

11. An apparatus as claimed in claim 10, in which the calculation means is arranged to determine the risk of pre-eclampsia by deriving the likelihood ratio for pre-eclampsia using a multivariate analysis based on distribution parameters derived from a set of reference data.

12. An apparatus as claimed in claim 11, in which the multivariate analysis is a multivariate Gaussian analysis.

13. An apparatus as claimed in any one of claims 10, 11 or 12, in which the apparatus further comprises (c) means for re-expressing the levels of each input screening marker as a multiple of the median level of the respective screening marker in unaffected pregnancies of the same gestational age as the fetus of the pregnant woman and supplying the re-expressed screening marker levels to said calculation means.

14. A kit for predicting the onset of pre-eclampsia in a pregnant woman, comprising means for assaying a sample from the woman for the levels of free β-human chorionic gonadotrophin (free β-hCG), Inhibin A and unconjugated oestriol (uE$_3$) present in the sample.

* * * * *